United States Patent [19]

Gathani

[11] Patent Number: 5,357,989
[45] Date of Patent: Oct. 25, 1994

[54] DENTAL CLEANSING MEMBER

[76] Inventor: Naresh Gathani, 35 Derwent Gardens, Wembley, Middx. HA9 8SG, United Kingdom

[21] Appl. No.: 920,488

[22] PCT Filed: Dec. 10, 1991

[86] PCT No.: PCT/GB91/02189
§ 371 Date: Mar. 11, 1993
§ 102(e) Date: Mar. 11, 1993

[87] PCT Pub. No.: WO92/10148
PCT Pub. Date: Jun. 25, 1992

[30] Foreign Application Priority Data

Dec. 10, 1990 [GB] United Kingdom ............... 9027022

[51] Int. Cl.5 ............................................ A61C 15/00
[52] U.S. Cl. .................................... 132/321; 132/329
[58] Field of Search ............... 132/321, 329; 424/7.1, 424/49; 433/215, 216

[56] References Cited

U.S. PATENT DOCUMENTS

| 3,247,857 | 4/1966 | Kanbar | 132/329 |
| 3,279,068 | 10/1966 | Stark | 424/7.1 |
| 3,491,776 | 1/1970 | Fleming | 132/321 |
| 4,359,455 | 11/1982 | Nakamura et al. | 424/7.1 |
| 4,364,927 | 12/1982 | Sipos et al. | 424/56 |
| 4,666,700 | 5/1987 | Frysh | 424/7.1 |
| 4,798,216 | 1/1989 | McCarty et al. | 132/321 |
| 4,976,951 | 12/1990 | Rosenberg et al. | 424/7.1 |
| 5,029,251 | 5/1993 | Curtis et al. | 132/321 |
| 5,033,488 | 7/1991 | Curtis et al. | 132/321 |

FOREIGN PATENT DOCUMENTS 2066074  7/1981  United Kingdom .

Primary Examiner—Gene Mancene
Assistant Examiner—Frank A. LaViola
Attorney, Agent, or Firm—William E. Pelton

[57] ABSTRACT

Dental floss or tape is impregnated and/or coated with a pH sensitive dye which changes color in an acid environment, thus alerting the user to the potential presence of dental caries. The floss or tape may incorporate a wax to restrict leaching of the dye.

8 Claims, No Drawings

DENTAL CLEANSING MEMBER

This invention relates to an improvement in dental cleaning and more particularly to a floss or tape etc. facilitating the detection of dental caries or a potential cariogenic environment.

Dental caries is caused by the presence of cariogenic bacteria in dental plaque which is nourished by various sugars in the diet. The metabolism of the sugars by the bacteria results in an acid attack on the tooth enamel resulting in demineralisation of the enamel. The demineralisation of enamel is always preceded by a change of neutral or alkaline pH to an acid pH in the dental plaque.

GB Patent 2066074, for example, discloses a method of introducing dental plaque of a dental caries patient into a pH sensitive aqueous solution containing colouring agents. This, however, forms part of a special test procedure.

According to the present invention, there is provided a dental cleansing strand member impregnated and/or coated with a pH-sensitive dye.

Such a strand member constitutes a dental caries diagnostic means which detects the presence of an acid pH plaque, thus immediately alerting the user to the presence or potential presence of dental disease. The warning is conveniently given by a quick visual check of the colour of the strand member after dental cleansing has taken place.

The strand member may comprise polyfilament dental floss or dental tape which is used every day for dental cleaning. This procedure is quick and simple and no special test procedure is necessary. Moreover there is no substantial increase in the cost of the floss or tape.

Upon being alerted, the user then takes the necessary oral hygiene measures to prevent further damage.

The dye used has one type of a colour in a certain pH range and changes to another colour in another pH range. The dye is nontoxic, edible and extremely pH sensitive in its range definition. The change of colour is obvious to the user thus alerting one to the presence of acid plaque and the potential for dental disease or indeed the presence of dental disease. The invention is not limited to polyfilaments of dental floss but can be applied to any other interstitial cleansing device such as dental tape.

The pH range of the indicators is between pH 6.8 and pH 3.0. Some examples of pH indicator dyes are haematoxylin, B.D.H full range, Gallein, B.D.H. 4.5, 2.5 Dinitro-Phenol, Allizarine Red S, Lacmoid, BDH 4080 and BDH soil, BDH Universal, Methyl Red, BDH 4460, Ethyl Red, Cochineal and Bromocresol purple.

Possible methods of incorporating the dye are:

A) By chemical bonding of the dye on to the floss filaments.

B) By physical bonding of the dye on to the floss filaments.

C) By the use of coatings impregnated with the dye for example coatings of starch gel and carboxy methyl cellulose. Wax can be used to stabilise the dye to prevent unwanted leaching of the dye.

I claim:

1. A dental cleansing strand member impregnated or coated with pH-sensitive dye, the pH sensitive dye producing a color change when exposed to an acid pH.

2. A member according to claim 1, wherein the pH-range of the dye is between 6.8 and 3.

3. A member according to claim 1, wherein the dye is chemically bonded to the strand member.

4. A member according to claim 1, wherein the dye is physically bonded to the strand member.

5. A member according to claim 1, wherein the member has a coating impregnated with the dye.

6. A member according to claim 1, further incorporating wax.

7. A member according to claim 1 in the form of dental floss.

8. A member according to claim 1 in the form of dental tape.

* * * * *